(12) United States Patent
Nakada et al.

(10) Patent No.: US 8,642,306 B2
(45) Date of Patent: Feb. 4, 2014

(54) FLOW CYTOMETER HAVING CELL-SORTING FUNCTION AND METHOD OF SEPARATING LIVING CELLS

(75) Inventors: Shigeyuki Nakada, Tamano (JP); Noriaki Kimura, Tamano (JP); Akihide Ito, Tokyo (JP); Kenji Yasuda, Tokyo (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 658 days.

(21) Appl. No.: 12/663,373

(22) PCT Filed: Jun. 11, 2008

(86) PCT No.: PCT/JP2008/060676
§ 371 (c)(1),
(2), (4) Date: Dec. 7, 2009

(87) PCT Pub. No.: WO2008/153056
PCT Pub. Date: Dec. 18, 2008

(65) Prior Publication Data
US 2010/0178682 A1    Jul. 15, 2010

(30) Foreign Application Priority Data
Jun. 14, 2007    (JP) .................................. 2007-157275

(51) Int. Cl.
*C12N 13/00*    (2006.01)

(52) U.S. Cl.
USPC .................. 435/173.9; 435/173.1; 435/173.4; 435/173.6; 435/173.7; 435/285.2; 435/288.7; 435/325

(58) Field of Classification Search
USPC ...................................... 435/173.7
See application file for complete search history.

(56) References Cited

U.S. PATENT DOCUMENTS

| | | | |
|---|---|---|---|
| 6,326,177 B1 * | 12/2001 | Schoenbach et al. | 435/173.7 |
| 6,582,899 B1 * | 6/2003 | Kamb et al. | 435/4 |
| 2004/0037815 A1 * | 2/2004 | Clarke et al. | 424/93.21 |

FOREIGN PATENT DOCUMENTS

| | | | |
|---|---|---|---|
| JP | 63126480 A | * | 5/1988 |
| JP | 2007-104929 | | 4/2007 |
| WO | WO-02-098501 | | 12/2002 |

OTHER PUBLICATIONS

Bakker Schut, TC et al. A new principle of cell sorting by using selective electroporation in a modified flow cytometer. Cytometry. 1990. 11: 659-666.*
JP 63126480, Sogawa et al. May 1998. English Translation, 20 pages.*
Takara Bio Inc., New Analysis and Separation Method for Stem Cells Using Ultra-High Speed Cell Sorter MoFlo™, Bio View, Apr. 2003, pp. 15-16, No. 42, Takara Bio Inc., Shiga, Japan.
Beebe et al., Nanosecond, high-intensity pulsed electric fields induce apoptosis in human cells, The FASEB Journal, Jun. 17, 2003, 17 (11): 1493-5.

* cited by examiner

*Primary Examiner* — Allison Ford
*Assistant Examiner* — Susan E Fernandez
(74) *Attorney, Agent, or Firm* — Global IP Counselors, LLP (57) ABSTRACT

A liquid sample flow containing living cells is irradiated with measurement laser light and the photo data of at least either scattering light or fluorescence that is generated by each of the living cells in the liquid sample flow due to the irradiation with the measurement laser light is acquired. Based on the photo data thus acquired, it is determined whether each of the cells assignable to the respective photo data is an unnecessary living cell or a target living cell. Based on the determination results, a pulse voltage is then applied exclusively to the living cells having been determined as unnecessary living cells so that the unnecessary living cells are damaged and killed.

15 Claims, 3 Drawing Sheets

FLOW CYTOMETER HAVING CELL-SORTING FUNCTION AND METHOD OF SEPARATING LIVING CELLS

CROSS-REFERENCE TO RELATED APPLICATIONS

This U.S. National stage application claims priority under 35 U.S.C. §119(a) to Japanese Patent Application No. 2007-157275, filed in Japan on Jun. 14, 2007, the entire contents of which are hereby incorporated herein by reference.

TECHNICAL FIELD

The present invention relates to a flow cytometer for processing a specific living cell in a group of living cells composed of the mixture of a plurality of unnecessary living cells and a plurality of target living cells. The present invention also relates to a living cell sorting method of separating the target cells from a group of living cells and collecting the sorted target cells.

BACKGROUND ART

The microscopes have been conventionally used for analyses of cells and chromosomes in a variety of researches (e.g., cancer). In the analyses using the microscopes, however, it has cost a great deal of time and effort for acquiring the large amount of data and statistically examining the data. In most of the analyses of cells and chromosomes, the flow cytometers are now used for analyzing a lot of samples (i.e., cells and chromosomes) in a short period of time and acquiring highly-reliable statistical data. The flow cytometers are capable of forming a flow of sample liquid containing sample particles (e.g., cells with antibodies being fluorescent-stained), irradiating laser light to the sample liquid flow, and measuring fluorescence and scattered light emitted from each of the large amount of the flowing sample particles. Accordingly, the flow cytometers are capable of acquiring highly reliable statistical data. In general, the flow cytometers of the type are used for the medical field research.

Now, medical treatment using stem cells (also called regenerative cells) is highly expected in the future medical field. In the physiological process (e.g., propagation and differentiation) of cells forming a biological body, the stem cells have both of a self-reproduction ability and an ability to differentiate into a type of cells having specific functions. In other words, the stem cells have a copying ability to increase the number of them and an ability to change themselves into different cells. A variety of cells are classified into the stem cells. Examples are: embryonic stem cells (ES cells) to be taken out of embryos; adult stem cells to be taken out of adults; and fetal stem cells to be taken out of fetuses. If it is possible to differentiate the stem cells into a type of cells suitable for an organ damaged by injury or illness, for instance, it is possible to transplant the differentiated cells to the damaged portions for the reproduction of the damaged cells. Therefore, the stem cells are now actively studied in a variety of fields including the regenerative medical field.

For taking the stem cells out of the embryonic stem cells or the fetal stem cells, the embryos or fetuses are required to be destroyed (i.e., kill), which is an ethical problem. In response to this, the adult stem cells are used as research targets for some of the present regenerative medical research. This is because the stem cells are obtainable from living humans (children or adults) without damaging their bodies. Obviously, the adult stem cells are necessary for the research of the adult stem cells. The adult stem cells are generally found in the bone marrow and the blood, the cornea and the retina of the eye, the liver, the skin and the like. However, chances are quite low to actually find out the adult stem cells therein. Therefore, even if the large amount of sample cells are obtained, only the small amount of adult stem cells can be found. For example, the mesenchymal stem cells exist in the bone marrow stromal cells. The mesenchymal stem cells can differentiate into a variety of tissues (e.g., the bone, the cartilage, the fat, the muscle, the tendon and the nerve). Accordingly, the mesenchymal stem cells have been attracting attention of the regenerative medical field for reproduction of tissues lost by illness or external damage. However, the mesenchymal stem cells only exist in the bone marrow at the rate of one to hundred thousand. Therefore, for reproduction of the lost tissues, it is necessary to increase the number of tissues by temporarily taking the tissues out of the body and subsequently culturing the taken-out tissues on the outside of the body. To this end, it is necessary to separate and extract the small amount of stem cells from a plurality of cells in the bone marrow. Sort and collection systems (cell sorters), employing the aforementioned flow cytometers, are now used for separating and extracting the small amount of adult stem cells from the large amount of sample cells in a shorter time.

Figure 4:
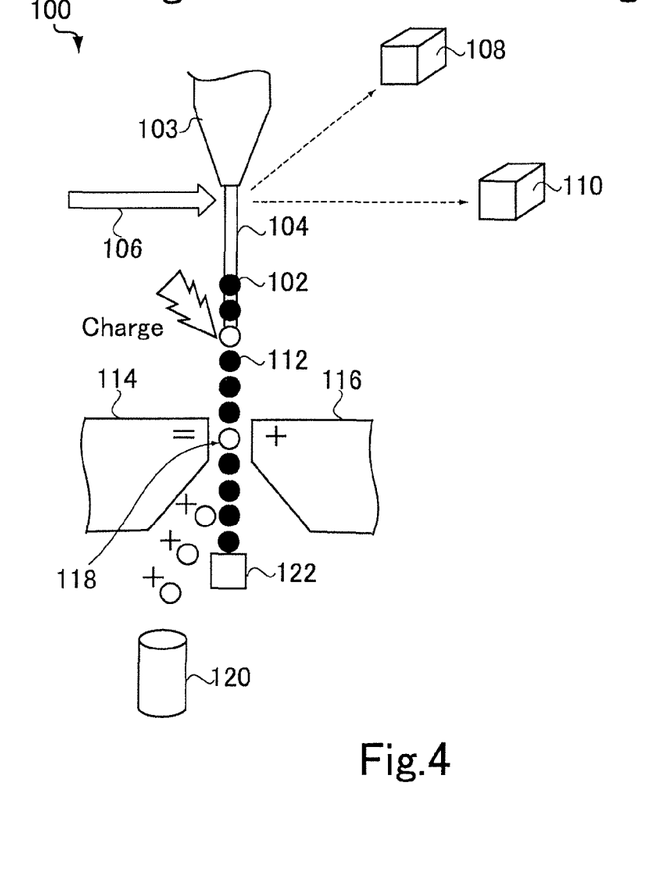
FIG. 4 is a schematic configuration diagram for illustrating a cell sorter, which is an example in the flow cytometer having a conventional cell sorting function.

For example, "New Analysis and Separation Method for Stem Cells Using Ultra-High Speed Cell Sorter MoFlo™" discloses an example of the cell sorter of the type. FIG. 4 is a schematic configuration diagram for illustrating a cell sorter disclosed in "New Analysis and Separation Method for Stem Cells Using Ultra-High Speed Cell Sorter MoFlo™". A cell sorter 100 is configured to discharge sample liquid which is ejected from a nozzle 103 as a jet flow 104. The sample liquid herein includes the large amount of sample cells 102. The large amount of sample cells 102 includes the small amount of stem cells. Therefore, the large amount of sample cells 102 is fluorescence-labeled for marking the stem cells. The cell sorter 100 irradiates measurement laser light 106 to the jet flow 104. In short, the cell sorter 100 is configured to sequentially irradiate the laser light 106 to the large amount of sample cells 102, respectively. Next, evaluation means (not illustrated in the figure), including photomultiplier tubes 108 and 110, obtains information of scattered light and fluorescence emitted from each of the large amount of sample cells 102. Then, the evaluation means (not illustrated in the figure) determines whether or not each of the sample cells, irradiated with the laser light 106, is among the stem cells (note a group of the sample cells, including a lot of stem cells, is specified in "New Analysis and Separation Method for Stem Cells Using Ultra-High Speed Cell Sorter MoFlo™"). The flow cytometers are generally configured as described above. However, the cell sorter 100 has a function of separating (i.e., sorting) the specified cells. For example, the cell sorter 100 is configured to vibrate the nozzle 103 at high frequency using a piezoelectric element (not illustrated in the figure). Accordingly, the jet flow 104 is forcibly changed into droplets 112. At the moment when a specific sample cell (e.g., a sample stem cell) enters a droplet 112 during forming the droplet 112, the droplet 112, including the specific sample cell, is positively (+) or negatively (−) charged (note the figure shows a positively-charged example).

The droplets 112 sequentially pass through a horizontal electric field 118 formed by two electric-field formation plate electrodes 114 and 116. In this case, only the falling direction of the charged droplets 112 is changed (i.e., deflected) by the horizontal electric field. Accordingly, the fallen droplets 112 are collected by a desired test tube 120. Thus, only the specific sample cells 102 (e.g., sample stem cells) are collected by the test tube 120. On the other hand, the other non-charged sample cells 102 fall in the vertical direction, and are accordingly collected by a waste liquid receiver 122.

DISCLOSURE OF THE INVENTION

Technical Problem

To change the sample liquid into the form of a jet flow as explained in "New Analysis and Separation Method for Stem Cells Using Ultra-High Speed Cell Sorter MoFlo™", however, the diameter of the outlet of the nozzle is required to be formed in extremely small size (e.g., 25 µm). In the example that is shown in "New Analysis and Separation Method for Stem Cells Using Ultra-High Speed Cell Sorter MoFlo™", cells, having the diameter of approximately a few µm to 20 µm, receive the physical shear force when passing through the small outlet. Therefore, the necessary stem cells have been damaged at high chances. Additionally, the necessary stem cells have been damaged at high chances by the high-frequency vibration in forcibly changing the jet flow into the droplets. Furthermore, when the droplets, including the sample cells, are charged and a high-electric field is applied thereto, the electric shock is even given to the necessary cells (e.g., the stem cells). Accordingly, a problem been occurred that the necessary cells (e.g., the stem cells) are even damaged. Even when the sample stem cells are separated out from the other cells using the aforementioned cell sorter and the sorted stem cells are differentiated into cells of a desired organ or the like, it is impossible to completely eliminate chances of occurrence of various and risky problems if the separated stem cells are damaged. For example, the differentiation of the stem cells may be inappropriate, or defective cells (e.g., cancer cells) may be developed. Consequently, the aforementioned cell sorters have not been still allowed to be used in the research field, where cells should be cautiously handled without being damaged.

Thus, in the field that cells are required to be cautiously handled, a predetermined sample cell, fallen and included in the droplet 112, has been separated and collected by moving the test tube 120 of the cell sorter 100 at a predetermined timing, for instance. However, the operable moving speed of the test tube 120 is extremely slower than the falling speed of the droplet 112 which is changed from the jet flow 104. When the large amount of samples flows at a high speed, only the extremely small amount of predetermined sample cells is obtainable among the large amount of sample cells. Additionally, when the flow speed of the samples is set to be extremely slower according to the moving speed of the test tube 120, it takes a plenty of time for separating and extracting the cells.

The present invention is provided in response to the aforementioned problems. It is an object of the present invention to provide a flow cytometer having a living cell sorting function for highly accurately distinguishing unnecessary living cells from a group of living cells including the large amount of living cells, and disposing them in a short period of time without damaging target living cells at all. Another object of the present invention is to provide a living cell sorting method of separating and collecting only target living cells from a group of living cells including the large amount of living cells. Yet another object of the present invention is to provide a living cell sorting method for separating only target living cells from a group of living cells including the large amount of living cells and subsequently culturing the separated target cells.

Solution to Problem to be Solved

The present invention provides a living cell sorting method to solve the aforementioned problems. The living cell sorting method includes the steps of:

forming a sample liquid flow including a group of living cells composed of mixture of a plurality of unnecessary living cells and a plurality of target living cells, the living cells flowing in a line and keeping away from each other;

irradiating measurement light toward the sample liquid flow;

obtaining light information of at least either of scattered light and fluorescence which is emitted by each of the living cells in the sample liquid flow when each of the living cells receives irradiation of the measurement light;

determining, based on the light information obtained in the obtaining step, whether each of the living cells corresponding to the light information is among either the unnecessary living cells or the target living cells, and damaging each of the unnecessary living cells and causing each of the unnecessary living cells to become a dead cell by generating a pulsed electric field at a portion of the sample liquid flow corresponding to each of the unnecessary living cells in response to a result of the determining step.

In the step of causing each of the unnecessary living cells to become a dead cell, each of the unnecessary living cells is herein preferably damaged and caused to become the dead cell by applying the pulsed electric field to each of the unnecessary living cells. Moreover, the pulsed electric field applied to each of the unnecessary living cells in the step of causing each of the unnecessary living cells to become a dead cell, is preferably configured to have pulse width for damaging DNA (deoxyribonucleic acid) in a cell nuclei of each of the unnecessary living cells by applying the pulsed electric field to the cell nuclei. In this case, the pulse width is preferably less than $1.0\times10^{-6}$ (second).

In the step of causing each of the unnecessary living cells to become a dead cell, each of the unnecessary living cells is preferably induced to apoptosis by Joule heat of pulsed electric current, and the pulsed electric current is generated in each of the unnecessary living cells by applying the pulsed electric field to each of the unnecessary living cells.

Also, the pulsed electric field applied to each of the unnecessary living cells, is preferably configured to have pulse width and peak voltage for irreversibly destroying a cell membrane of each of the unnecessary living cells under a condition that an electric field applied to a cell membrane is higher than an electric field applied to a cell nuclei of each of the unnecessary living cells in the step of causing each of the unnecessary living cells to become a dead cell. In this case, the pulse width is preferably equal to or greater than $1.0\times10^{-6}$ (second). The electric field, applied to the cell membrane of each of the unnecessary living cells, is preferably equal to or greater than 1 kV/cm, and the peak voltage is preferably equal to or greater than 10V.

Furthermore, the living cell sorting method preferably includes the steps of: collecting the sample liquid in a collection container after the pulsed voltage is applied, the sample liquid including the target living cells and the damaged and dead cells by applying the pulsed voltage; and separating and taking out a cell floating in the sample liquid without attaching to a surface of an inner wall of the collection container as the dead cell and simultaneously collecting a cell attaching to the surface of the inner wall of the collection container in the sample liquid as one of the target living cells.

Furthermore, the living cell sorting method preferably includes the steps of:

collecting the sample liquid in a collection container after the pulsed voltage is applied, the sample liquid including the target living cells and the dead cells damaged by applying the pulsed voltage; and reducing dead cell ratio of the sample liquid by culturing only the target living cells in the sample liquid by executing a culture processing to the sample liquid in the collection container, the culturing processing being capable of culturing the living cells.

Also, the present invention provides a flow cytometer having a cell sorting function. The flow cytometer includes a flow cell, an electric field generation section, a measurement light irradiation section, a light information obtainment section, a living cell determination section and a control section. A sample liquid flows in the interior of the flow cell. The sample liquid includes a group of living cells, composed of mixture of a plurality of unnecessary living cells and a plurality of target living cells. The electric field generation section is configured to generate a pulsed electric field on a specific area in the flow cell. The measurement light irradiation section is configured to irradiate measurement light toward a flow of the sample liquid in the interior of the flow cell. The light information obtainment section is configured to obtain light information of at least either of scattered light and fluorescence which is emitted from each of the living cells in the flow of the sample liquid when each of the living cells receives irradiation of the measurement light. The living cell determination section is configured to determine whether each of the living cells, corresponding to one of the light information of the living cells, is either among the unnecessary living cells or the target living cells based on the light information obtained by the light information obtainment section. The control section is configured to control timing of generating the pulsed electric field by the electric field generation section in accordance with a result of the determination by the living cell determination section. Additionally, the control section is configured to control the electric generation section to generate the electric field on the specific area at timing when each of the unnecessary living cells passes through the specific area in the flow cell and each of the unnecessary living cells is damaged and caused to become a dead cell.

In this case, the electric field generation section is preferably composed of two electrodes and a pulsed voltage application section. The electrodes are disposed for interposing the specific area of the flow cell therebetween. The pulsed voltage application section is configured to apply the pulsed voltage to an area between the electrodes.

Advantageous Effects of Invention

According to the flow cytometer having a cell sorting function, it is possible to highly accurately distinguish the unnecessary living cells from the group of living cells including the large amount of living cells in a short period of time without damaging the target living cells at all, and it is further possible to cause the unnecessary living cells to become the dead cells by damaging them. Additionally, according to the living cell sorting method, it is possible to highly accurately separate and collect the target living cells from the group of living cells including the large amount of living cells in a short period of time without damaging the target living cells at all. Moreover, according to the living cell sorting method of the present invention, it is possible to highly accurately separate the target living cells from the group of living cells including the large amount of living cells and culture the separated target living cells in a short period of time without damaging the target living cells at all.

BEST MODE FOR CARRYING OUT THE INVENTION

Figure 1:
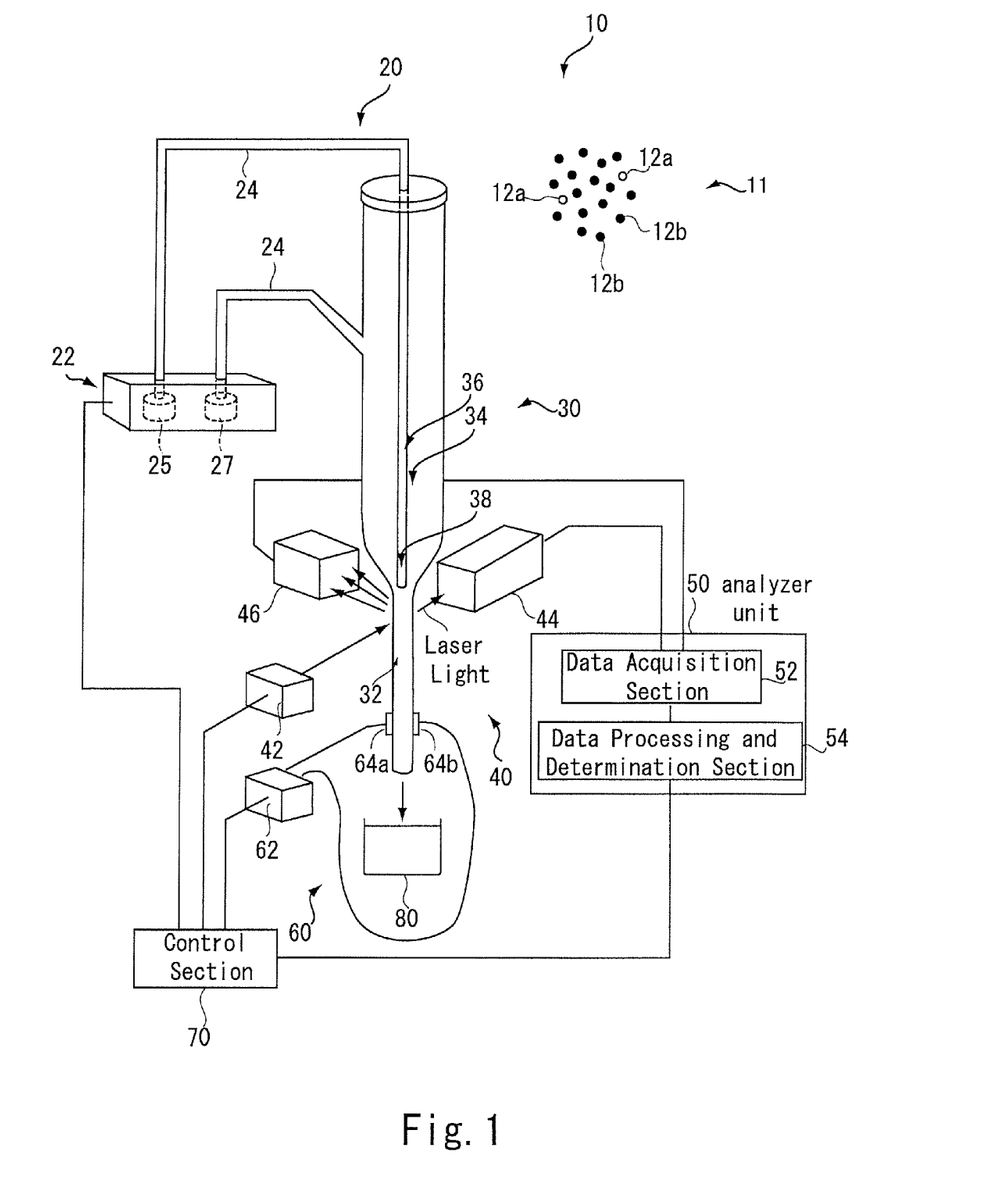
FIG. 1 is a schematic perspective diagram for illustrating an example of a flow cytometer having a cell sorting function according to the present invention.

Following is detailed explanation of a flow cytometer having a cell sorting function and a cell sorting method according to the present invention, based on a preferred example illustrated in the attached figures. FIG. 1 illustrates a schematic perspective view of a flow cytometer 10, an example of a flow cytometer, having a cell sorting function, of the present invention.

The flow cytometer 10 is composed of a liquid flow formation unit 20, an optical unit 40, an analyzer unit 50, a voltage application unit 60, a control section 70 for controlling operational sequences of the components, and a collection container 80. The flow cytometer 10 is an apparatus operable as follows. The flow cytometer 10 firstly determine whether or not each cell in a group of living cells is a stem cell. The group of living cells is herein composed of mixture of the small amount of stem cells (i.e., target living cells) and the large amount of unnecessary cells (i.e., remaining other cells excluding the stem cells). Then, the flow cytometer 10 applies pulsed voltage only to the living cells, which are determined as non-stem cells (i.e., unnecessary living cells). The flow cytometer 10 thus damages and kills the unnecessary cells. Additionally, the flow cytometer 10 includes the collection container 80. The collection container 80 collects the sample liquid including the stem cells and the dead cells after the application of the pulsed voltage. Furthermore, the flow cytometer 10 has a function of selectively collecting cells which floats in the sample liquid without attaching to the surface of the inner wall of the collection container 80, as dead cells. The flow cytometer 10 also has a function of reducing the ratio of the dead cells in the sample liquid. In this case, the function is achieved by selectively culturing only the stem cells in the sample liquid in the collection container 80 through the culturing process for culturing the living cells.

The flow cytometer 10 is an apparatus having a so-called sorting function (i.e., a sorting system). The sorting function is to separate the stem cells from a group of living cells (e.g., a group of living cells extracted from human bone marrow) in which the stem cells are included (highly-possibly included) in the large amount of living cells at small ratio. In the present embodiment, with the flow cytometer 10, the stem cells are thus separated from the group of living cells (e.g., a group of living cells extracted from the human bone marrow) in which the stem cells are included (highly-possibly included) at small ratio in the large amount of the living cells, and a variety of processing are subsequently executed for the separated stem cells. Note the target living cells are not limited to the stem cells in the present embodiment.

As described above, the so-called mesenchymal stem cells slightly exist in the human bone marrow at the ratio of one to hundred thousand. In the cell sort to be executed using the flow cytometer 10, staining processing (fluorescent labeling) is preliminarily uniformly executed for the group of living cells using fluorescent staining dye. Accordingly, the stem cells and the other unnecessary living cells are characterized for discriminating them from each other. The stem cells have a characteristic of discharging the staining dye introduced thereinto by the agency of so-called MDR (multi-drug resistance). When the staining processing is executed for a group of living cells using specific fluorescent staining dye under a predetermined condition, little or no stem cells are stained due to the MDR function (i.e., almost the stem cells discharge the staining dye). In this way, a group of living cells 11 is used for the cell sort to be executed by the flow cytometer 10. In the group of living cells 11, stem cells 12a and other unnecessary cells 12b are characterized for discriminating them from each other based on a difference in a staining state of fluorescent staining dye between the stem cells 12a and the unnecessary cells 12b. Obviously, it is not clear whether each cell of the group of living cells 11 is either the stem cell 12a or the unnecessary living cell 12b at the time of introducing the group of living cells 11 into the flow cytometer 10. In the specification of the present application, both of the stem cells 12a and the unnecessary living cells 12b are described as an analysis sample 12 (especially when it is not clear whether a cell is either the stem cell or the unnecessary cell). In the present embodiment, the stem cells and the other unnecessary living cells are discriminably characterized from each other, using the MDR function of the stem cells. In the present invention, however, the method of discriminably characterizing the target cells and the other unnecessary living cells with use of the fluorescent staining dye is not particularly limited.

The liquid flow formation unit 20 is composed of a liquid supply device 22 and a flow tube section 30. The liquid supply device 22 and the flow tube section 30 are connected through pipes 24. The liquid supply device 22 accommodates an analysis sample liquid tank 25 and a sheath liquid tank 27. The analysis sample liquid tank 25 stores analysis sample liquid, whereas the sheath liquid rank 27 stores sheath liquid. The flow tube section 30 includes a flow cell 32, an outside tube path 34 and a sample liquid flow tube 36. The sample liquid flows through the interior of the flow cell 32 while it is enclosed by the sheath liquid. The outside tube path 34 is connected to the flow cell 32 for providing the flow cell 32 with the sheath liquid. The sample liquid tube 36 is disposed in the interior of the outside tube path 34 for providing the flow cell 32 with the sample liquid. The sample liquid tank 25 of the liquid supply device 22 is connected to the sample liquid flow tube 36 through one of the pipes 24, whereas the sheath liquid tank 27 of the liquid supply device 22 is connected to the outside tube path 34 through the other of the pipes 24. The collection container 80 is provided at the outlet of the flow cell 32.

In the liquid supply device 22, each of the tanks is provided with an air pump (not illustrated in the figure). The flow cytometer 10 is configured to control the air pump (not illustrated in the figure) to pressurize the interior of the sheath liquid tank 27. Accordingly, the sheath liquid is supplied to the interior of the outside tube path 34 from the sheath liquid tank 27, and a sheath flow 15 is formed (see FIG. 2). The sheath flow 15 flows through the outside tube path 34 and the flow cell 32 from top to bottom in FIG. 1.

Additionally, the flow cytometer 10 is configured to control the air pump (not illustrated in the figure) to pressurize the sample liquid tank 25. Accordingly, the sample liquid is supplied to the sample liquid flow tube 36 from the sample liquid tank 25. The supplied sample liquid is discharged from a discharge port 38 into the sheath flow 15. Note the discharge port 38 is a bottom opening end of the sample liquid flow tube 36 in FIG. 1.

In the flow cell 32, the flow of the sample liquid is hydrodynamically narrowed down when the sample liquid is discharged into the sheath flow 15. Accordingly, a flow of the sample liquid enclosed by the sheath flow 15 will be narrow, and a sample liquid flow 17 is thus formed. In the sample liquid flow 17, the analysis samples 12 are flow-directionally aligned in a line while separated from each other. In the flow cytometer 10 of the present embodiment, operations of the liquid supply device 22 and the like (e.g., pressure of the air pumps) are regulated for separately flowing the analysis samples 12 (e.g., sample liquid flow) at predetermined approximately equal intervals (e.g., 10 μm). In the flow cell 32, the analysis samples 12 are specifically aligned in a line. The analysis samples 12 sequentially flow through the flow cell 32 at predetermined velocity V (m/sec.) on a one-by-one basis. A measurement laser light irradiation section 42 of the optical unit 40 irradiates laser light toward the flow cell 32. The analysis samples 12 sequentially flow on a one-by-one basis while passing through the laser light beam.

The optical unit 40 includes the measurement laser light irradiation section 42 and light receivers 44 and 46. The measurement laser light irradiation section 42 is configured to irradiate measurement laser light toward the flow cell 32. The light receiver 44 is configured to receive scattered light from each analysis sample 12 flowing through the flow cell 32 (while included in the sample liquid flow 17). The light receiver 44 is subsequently configured to output a signal in accordance with the received scattered light. On the other hand, the light receiver 46 is configured to receive fluorescence emitted by each analysis sample 12 flowing through the flow cell 32. The light receiver 46 is subsequently configured to output a signal in accordance with the received fluorescence. The light receivers 44 and 46 are connected to the analyzer unit 50. The outputted light signals are transmitted to the analyzer unit 50.

Figure 2:
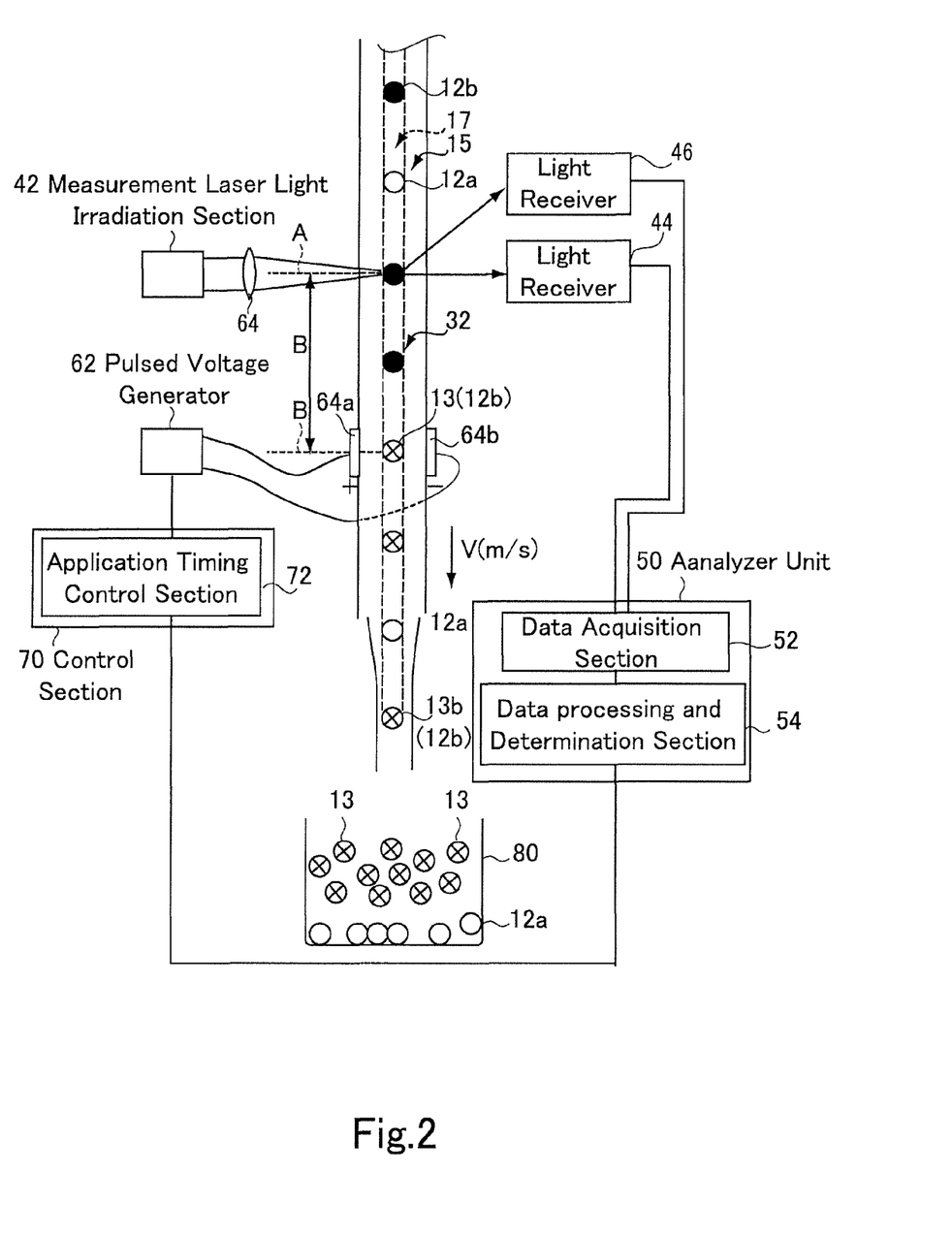
FIG. 2 is a schematic side view of the flow cytometer illustrated in FIG. 1 for more detailedly illustrating configurations and operations of an optical unit and a voltage application unit thereof.

FIG. 2 is a schematic lateral view for more detailedly illustrating configurations and operations of the optical unit 40 and the voltage application unit 60. The optical unit 40 is composed of the measurement laser light irradiation section 42 and a laser light shape and adjustment section 64. The measurement laser light irradiation section 42 is configured to irradiate laser light of predetermined wave length toward the sample liquid flow 17 flowing through the flow cell 32. The laser light shape and adjustment section 64, composed of a lens and the like, is configured to shape the measurement laser light irradiated by the measurement laser light irradiation section 42 and guide it to the sample liquid flow 17 in the interior of the flow cell 32. The measurement laser light irradiation section 42 is connected to a laser power source (not illustrated in the figure). The measurement laser light irradiation section 42 is configured to continuously irradiate measurement laser light toward the sample liquid flow 17, which flows through the flow cell 32 and includes the analysis samples 12 aligned in a line, under the control of the control section 10. The measurement laser light, irradiated by the measurement laser light irradiation section 42, is laser light of a predetermined wave length for generating fluorescence of predetermined wave length range by exciting fluorescent pigments attaching to the analysis samples 12 (especially the fluorescent pigments captured into the unnecessary living cells 12b). Note a heretofore known laser device (e.g., a solid-state laser and a semiconductor laser) may be used as the measurement laser light irradiation section 42.

The light receiver 44 is opposed to the measurement laser light irradiation section 42, while the flow cell 32 is interposed therebetween. The light receiver 44 is configured to continuously receive front scattered light of laser light from the analysis sample 12 which passes through the flow cell 32, and output an analogue electric signal in accordance with luminosity of the received front scattered light. On the other hand, the light receiver 46 is disposed vertically to an irradiation direction of the laser light irradiated by the laser light irradiation section 42. The light receiver 46 is also disposed vertically to a moving direction of the analysis sample 12 in the outside tube path 30. The light receiver 46 is configured to receive fluorescence, emitted by the analysis sample 12 when the laser light is received by the analysis sample 12, and output an analogue electric signal in accordance with luminosity of the received fluorescence. For example, PMT (photomultiplier tube) may be used for the light detection and output of an analogue signal in the light receivers 44 and 46.

The analyzer unit 50 is composed of a data acquisition section 52 and a data processing and determination section 54. The data acquisition section 52 is configured to receive an analogue signal outputted by the light receivers 44 and 46, execute AD conversion of the analogue signal, and output a digital signal obtained by the AD conversion. The data processing and determination section 54 is configured to process the digital information outputted by the data acquisition section 52, and generate information (stained amount information) representing a stained level of each of the analysis samples 12 (degree of the amount of fluorescent pigments in a living cell), for instance. The data processing and determination section 54 is further configured to determine whether the analysis sample 12, corresponding to the stained amount information, is either the unnecessary living cell or the stem cell based on the stained amount information. In the present embodiment, as described above, the stained level (i.e., degree of the fluorescent pigments in a living cell) of the stem cell 12a is lower than that of the unnecessary living cell 12b. Accordingly, the analysis sample 12, corresponding to the stained amount information representing a relatively low stained level (e.g., a value of the stained amount is equal to or less than a predetermined threshold), is determined as the stem cell 12a.

The data processing and determination section 54 is configured to transmit a result of the determination to an application timing control section 72 (timing control section 72) of the control section 70. Note output devices (not illustrated in the figure), such as a display and a printer, are connected to the analyzer unit 50. Accordingly, the output devices are allowed to display and output computation results by the data processing and determination section 54. In the present embodiment, it is determined whether the analysis sample 12 is either the stem cell or the unnecessary cell, based on the stained degree of the cell which is estimated from the light information. However, the criterion for determining whether the living cell is either the stem cell or the unnecessary living cell, used in the determination of the type of the living cell in the present invention, is not particularly limited. Additionally, contents of the processing to be executed to the light information (e.g., the obtained fluorescence information) and the algorithm for specifying the target living cell, both of which are used in the determination of the type of the living cells in the present invention, are not particularly limited.

The voltage application unit 60 is composed of a pulsed voltage generator 62 and electrodes 64a and 64b. The electrodes 64a and 64b are disposed on the tube wall of the flow cell 32, while opposing to each other. Additionally, the electrodes 64a and 64b are connected to output terminals of the pulsed voltage generator 62, respectively. The pulsed voltage generator 62 is configured to apply pulsed voltage in the area between the electrodes 64a and 64b under the control of the application timing control section 72 of the control section 70. The pulsed voltage generator 62 is heretofore known pulsed voltage generation means, and is capable of outputting pulsed voltage with the pulse width of roughly $1.0 \times 10^{-9}$ to $1.0 \times 10^{-6}$ (second), for instance.

The electrodes 64a and 64b are disposed in sufficiently remote positions (e.g., remote positions at the distance of 1.0 mm or greater) from an irradiation position A (see FIG. 2) of the measurement light toward the flow-directionally downstream of the sample liquid flow 17. For example, when an electrode position B (see FIG. 2), corresponding to the center parts of the electrodes 64a and 64b, is away from the irradiation position A of the measurement laser light by a preliminarily-set distance D (m) and velocity of the sample liquid flow 17 (i.e., velocity of the analysis sample 12) is V (m/second), a single analysis sample 12 is assumed to pass through the electrode position B when it elapses "T=D/V (seconds)" after the analysis sample 12 receives measurement laser light. Before it elapses at least T (second) since the obtainment of the light information, the analyzer unit 50 is configured to finish determining whether the analysis sample, corresponding to the obtained light information, is either the unnecessary living cell or the stem cell, and transmitting a result of the determination to the application timing control section 72.

When the application timing control section 72 receives a result of the determination, representing that the analysis sample 12 irradiated with the measurement laser light is the unnecessary living cell 12b, from the data processing and determination section 54 of the analyzer unit 50, the application timing control section 72 is configured to control an operation of the pulsed voltage generator 62 for applying pulsed voltage to the unnecessary living cell 12b. On the other hand, when the application timing control section 72 receives a result of the determination, representing that the analysis sample 12 irradiated with the measurement laser light is the stem cell 12a, from the data processing and determination section 54 of the analyzer unit 50, the application timing control section 72 is configured to control an operation of the pulsed voltage generator 62 for not applying pulsed voltage to the stem cell 12a.

Specifically, when the application timing control section 72 receives a result of the determination, representing that the analysis sample 12 irradiated with the measurement laser light is the unnecessary living cell 12b, from the data processing and determination section 54 of the analyzer unit 50, the application timing control section 72 is configured to control the pulsed voltage generator 62 to apply voltage (i.e., to apply pulsed voltage to the area between the electrodes 64a and 64b) only in a predetermined period of time (i.e., a period of time when the corresponding analysis sample 12 reliably passes through an effective electric field area E to be described). Additionally, the application timing control section 72 is configured to control the pulsed voltage generator 62 not to apply pulsed voltage in the predetermined period of time (i.e., the period of time when the corresponding analysis sample 12 reliably passes through the effective electric field area E to be described), while it receives a result of the determination, representing that the analysis sample 12 irradiated with the measurement laser light is the stem cell 12a, from the data processing and determination section 54 of the analyzer unit 50.

The aforementioned predetermined period of time may be preliminarily set. For example, when the information of "T=D/V (seconds)" and the information of the size of the effective electric field area E to be described (see FIG. 3) have been preliminarily set for the application timing control unit 72 and the application timing control unit 72 has relatively high processing performance, application of the pulsed voltage may be controlled as follows. For example, the application timing control section 72 is configured to estimate the timing when the analysis sample 12 (i.e., the stem cell 12a), corresponding to the determination result, passed through the irradiation position A of the measurement laser light based on the timing when the application timing control section 72 received the transmitted determination result while the processing time required for the analyzer unit 50 is taken into consideration. Additionally, when the application timing control section 72 receives a result of the determination representing that the analysis sample 12 is the stem cell 12a, the application timing control section 72 is configured to at least identify the timing when it elapses "T=D/V (seconds)" since the aforementioned estimated timing (i.e., the timing when the corresponding analysis sample 12 passes through the electrode position B). Moreover, the application timing control section 72 is configured to compute a predetermined period of time, including the passage timing in the electrode position B (i.e., a period of time when a single corresponding analysis sample 12 passes through the effective electric field area E), based on the size of the effective electric field area E. When the application timing control section 72 receives a result of the determination representing that the analysis sample 12 is the stem cell 12a, the application timing control section 72 is configured to control the pulsed voltage generator 62 not to apply pulsed voltage at least in the predetermined period of time (i.e., the period of time when the corresponding analysis sample 12 reliably passes through the effective electric field area E to be described).

Figure 3A:
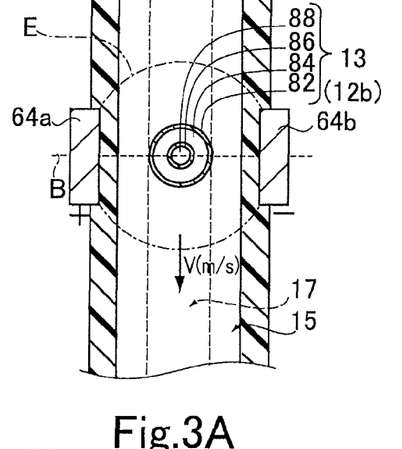
FIG. 3 is composed of enlarged schematic side views 3(a) and 3(b) of electrodes and periphery thereof which are provided in the flow cell of the flow cytometer illustrated in FIG. 1.
Figure 3B:
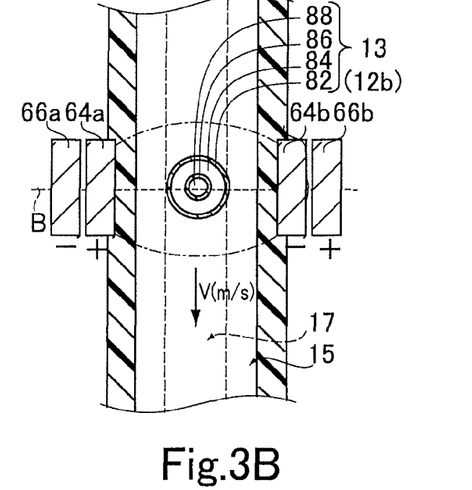

FIGS. 3(a) and 3(b) illustrate pulsed voltage application to the unnecessary living cell 12b moving though the flow cell 32. FIGS. 3(a) and (b) are enlarged views of the vicinity of the electrodes 64a and 64b of the flow cell 32 illustrated in FIG. 2. The electrodes 64a and 64b are fixed to the tube wall of the flow cell 32. When the electrodes 64a and 64b make contact with the sheath liquid of the sheath flow 15, for instance, electrolysis occurs intensely in the sheath liquid and the sample liquid. The electrolysis reactions may even damage the necessary living cells (i.e., the stem cells 12a) in the interior of the flow cell 32. Therefore, the electrodes 64a and 64b indirectly make contact with the sheath liquid and the sample liquid through an insulator without directly making contact with them. In FIGS. 3(a) and 3(b), the electrodes 64a and 64b are fixed to the tube wall of the flow cell 32 while they are partially buried in the tube wall of the flow cell 32. For example, a part of the tube wall of the flow cell 32, made of an insulator (e.g., quartz), is interposed between the sheath liquid and the electrodes 64a and 64b.

In the present embodiment, the electrodes for applying the pulsed voltage are composed of the two opposed electrodes 64a and 64b, and have so called the dipole structure, as illustrated in FIG. 3(a). When the pulsed voltage generator 62 applies pulsed voltage to the area between the electrodes 64a and 64b, an electric field is generated in the area. Both the sheath liquid of the sheath flow 15 and the sample liquid of the sample liquid flow 17 have conductivity, and an electric field is generated in the interior of the flow cell 32. For example, when the pulsed voltage having the pulse width of roughly $1.0 \times 10^{-9}$ to $1.0 \times 10^{-6}$ (second) is applied so that the electrode 64a has a higher electric potential and the electrode 64b has a lower electric potential, an electric field (i.e., pulsed electric field) having the pulse width of roughly $1.0 \times 10^{-9}$ to $1.0 \times 10^{-6}$ (second) is generated, in which electric flux lines direct from the electrode 64a to the electrode 64b.

When an electric field is applied to the area between the electrodes forming the dipole structure illustrated in FIG. 3(a), the effective electric field area E, having sufficient intensity for causing the living cells to become the dead cells, is formed in the interior of the flow cell 32 while the area is spread about the electrode position B to some extent. The effective electric field area E is formed in sufficiently small size so that any other samples 12 cannot exist in the effective electric field area E while a single analysis sample 12 passes through it. For example, when velocity of the analysis sample 12 (i.e., flow velocity of the sample liquid flow 17) is set to 5.0 (m/second) and the number of the analysis samples 12 flowing in a second is set to be 5000, average of distance between adjacent analysis samples 12 in the sample liquid flow 17 is $1.0 \times 10^{-3}$ (m). In this case, the size of the electrodes 64a and 64b and the magnitude of the electric field to be applied are adjusted for setting the length of the effective electric field area E along the flow direction of the sample liquid sufficiently to be smaller than $1.0 \times 10^{-3}$ (m). In the present invention, as illustrated in FIG. 3(b), a so-called multiple electrodes structure may be formed by providing electric-field adjustment electrodes 66a and 66b in addition to the electrodes 64a and 64b for applying pulsed voltage in order to prevent extension of the effective electric area E along the flow direction of the sample liquid.

When the pulsed electric field of sufficiently high intensity acts on the unnecessary living cell 12b moving through the flow cell 32, the unnecessary living cell 12b is damaged and is caused to become the dead cell. There are mainly two approaches how to cause the unnecessary living cell 12b to become the dead cell by the action of the pulsed electric field on (i.e., by the application of the pulsed voltage to) the unnecessary living cell 12b. According to the first approach, the electric field is concentrated on a cell membrane 82 of the unnecessary living cell 12b by the application of the pulsed voltage having the relatively broad pulse width equal to or greater than $1.0 \times 10^{-6}$ (second). Accordingly, an irreparable hole is generated in the cell membrane 82, and the unnecessary living cell 12b is caused to become the dead cell. In short, when the irreparable hole is generated in the cell membrane 82, a cell cytoplasm 84 flows to the outside through the hole and the unnecessary living cell 12b accordingly dies. According to the second approach, on the other hand, the electric field acts even on (in other words, breaks in) a cell nuclei 88 of the unnecessary living cell 12b by the application of the pulsed voltage having the relatively narrow pulse width less than $1.0 \times 10^{-6}$ (second). Accordingly, the DNA (deoxyribonucleic acid), included in the cell nuclei 88, is damaged and the unnecessary living cell 12b is caused to become the dead cell. According to the second approach, it is possible to cause the unnecessary living cell 12b to become the dead cell by inducing apoptosis originally programmed in the DNA. In this case, the pulsed electric field of sufficiently high intensity acts on the unnecessary living cell 12b. Therefore, the pulsed electric current, corresponding to the pulsed electric field, especially flows through the cell nuclei 88 in the unnecessary living cell 12. Accordingly, the DNA is damaged by the Joule heating, generated by the pulsed electric current. This results in apoptosis of the unnecessary living cell 12.

The unnecessary living cell 12b and the stem cell 12a, which are general cells, have the following structure, respectively. The nuclei and the cytoplasm 84 are enclosed by the cell membrane 82, and a cell nucleus 88 is enclosed by a nuclear envelope 86 in the nuclei. Chromosomes, respectively including the DNA, exist in the nucleoplasm 88. When the unnecessary living cell 12b is illustrated as an equivalent electric circuit, the cell membrane 82 and the nuclear envelope 86 can be illustrated as a resistance and a capacitor. Electric permittivity of the capacitor is herein relatively high. In short, the cell membrane 82 and the nuclear envelope 88 mainly operate as a capacitor in the equivalent electric circuit of the unnecessary living cell 12b of this type. When the pulse width, applied to the entire equivalent circuit of this type, is broad (i.e., when frequency of the applied voltage is low), the capacitor accumulates electric charges and relatively high voltage accordingly operates. On the other hand, when the pulse width becomes narrower (i.e., when frequency of the applied voltage becomes higher), voltage acts on the entire equivalent circuit while the capacitor does not accumulate electric charges. This is similarly true for the unnecessary living cell 12b. When the pulsed voltage, having the relatively broad pulse width equal to or greater than $1.0 \times 10^{-6}$ (second), is applied, the electric field focuses on the cell membrane 82 of the unnecessary living cell 12b as the aforementioned first approach. On the other hand, when the pulsed voltage, having the relatively narrow pulse width less than $1.0 \times 10^{-6}$ (second), is applied, the electric field acts even on (in other words, electric energy breaks in) the cell nuclei 88 of the unnecessary living cell 12b as the aforementioned second approach.

Even if a hole is herein formed in the cell membrane 82 by concentrating the electric field on it just like the first approach and the electric field is relatively small, the cell membrane 82 repairs the hole formed therein with its own self-repairing function in a short period of time. In other words, when a hole is formed in the cell membrane 82 just like the first configuration and the electric field acting on the cell membrane 82 is relatively small, it is impossible to cause the unnecessary living cell 12b to become the dead cell. When the unnecessary living cell 12b is caused to become the dead cell by forming a hole in the cell membrane 82 just like the first approach, it is necessary to form a hole that cannot be repaired with the self-repairing function of the cell. It is necessary to apply a sufficiently strong electric field enough to destroy tissues of the cell membrane 82. In the present invention, when the pulsed voltage, having the relatively broad pulse width equal to or greater than $1.0 \times 10^{-6}$ (second), is applied, it is preferable to set the electric field acting on the cell membrane 82 to be equal to or greater than 1 kV/cm. The diameter of the general flow cell is 100 to 400 (μm), which means that the distance between the electrodes for applying the pulsed voltage is set to 100 to 400 (μm). Therefore, it is preferable to set the peak value of the pulsed voltage to be equal to or greater than 10 (V), for instance. When the electric field, acting on the sample liquid and the sheath liquid, is too strong, a shock wave may occur or the sample liquid and the sheath liquid may suddenly boil. Accordingly, the flow cell may be destroyed. It is preferable to set the peak value of the pulsed voltage to be equal to or less than 1000 (V) for preventing damage and destruction of the device. In other words, when the pulsed voltage, having the relatively broad pulse width equal to or greater than $1.0 \times 10^{-6}$ (second), is applied in the present invention, it is preferable to set the peak value of the pulsed voltage to be equal to or greater than 10 (V) and equal to or less than 1000 (V), for instance.

According to the aforementioned second approach, apoptosis originally programmed in the DNA is induced, for instance, and the unnecessary living cell 12b is accordingly caused to become the dead cell. Apoptosis is a type of death of a cell forming a part of a body of a multicellular organism. Apoptosis is referred to as managed and regulated suicide of a cell, which is actively caused for maintaining the individual body in a good condition. In contrast to apoptosis, cell death, caused by environmental deterioration of the inside and the outside of a cell due to poor blood circulation and external injury, is referred to as necrosis or mortification. A type of cell death, caused by a hole irreversibly formed in the cell membrane as seen in the aforementioned first approach, is categorized as necrosis.

For inducing apoptosis in a cell, the DNA is required to be damaged. According to the second approach, an electric field is controlled to be applied even to (in other words, an electric field is controlled to break in) the cell nuclei 88 of the unnecessary living cell 12b by applying the pulsed voltage having the relatively narrow pulse width less than $1.0 \times 10^{-6}$ (second), thereby damaging the DNA (deoxyribonucleic acid) included in the cell nuclei 88. In the second approach, it is preferable to set the pulse width to be as narrow as possible, i.e., less than $1.0 \times 10^{-7}$ (second), for applying a large electric field to the cell nuclei 88, in other words, for making electric energy break in the deep portion of the unnecessary living cell 12b.

According to the present invention in which a living cell is damaged and is caused to become a dead cell by the application of the pulsed voltage, it is possible to cause a cell to become a dead cell by a single pulsed voltage having sufficiently narrow pulse width (e.g., $1.0 \times 10^{-9}$ to $1.0 \times 10^{-6}$ (second)). In other words, it is possible to cause a cell to become a dead cell per a pulse. For example, when the pulsed voltage having the pulse width of $1.0 \times 10^{-9}$ (second) is applied, it is possible to maximally cause the cells of the number of $1.0 \times 10^{9}$ to become the dead cells in a second. When a pulsed voltage generation device continuously outputs the pulsed voltage, each pulsed voltage is inhibited to a relatively low level when the pulse width becomes narrower (i.e., when the frequency becomes higher). As described above, in the flow cytometer 10, the electrodes 64a and 64b are provided in the tube wall of the quite thin flow cell 32 having the diameter of 100 to 400 (μm), and the pulsed voltage is applied to the area between the quite adjacent electrodes 64a and 64b having the inter-electrode distance of 100 to 400 (μm). Accordingly, even if each pulsed voltage is inhibited to a relatively low level, it is possible to make the intensity of the electric field to be generated between the electrodes sufficiently large enough to cause a living cell to become a dead cell.

According to the flow cytometer 10, when the application timing control section 72 receives a result of determination, representing that the analysis sample 12 irradiated with measurement laser light is the unnecessary living cell 12b, from the data processing and determination section 54 of the analyzer unit 50, the pulsed voltage generator 62 is operated to apply the pulsed voltage to the unnecessary living cell 12b. Accordingly, the unnecessary living cell 12b of the sample group 12 is reliably caused to become a dead cell. On the other hand, when the application timing control section 72 receives a result of determination, representing that the analysis sample 12 irradiated with measurement laser light is the stem cell 12a, from the data processing and determination section 54 of the analyzer unit 50, the pulsed voltage generator 62 is operated not to apply the pulsed voltage to the stem cell 12a. Accordingly, the stem cell 12a of the sample group 12 reliably passes through the effective electric field area E without being damaged at all.

After passing through the effective electric field area E, the sample 12 falls into the collection container 80. For example, the living cells generally have a characteristic of attaching to (implanting into) an object that the living cells make contact with. Because of this, the analysis samples 12, which were not caused to become the dead cells 13 by the application of the pulsed voltage, that is, only the stem cells 12a, attach to the wall surface of the collection container 80. On the other hand, the cells, which were caused to become the dead cells 13 by the application of the pulsed voltage, float in the sample liquid in the collection container 80. It is possible to separate and collect only the stem cells 12a, which are the target living cells, in the collection container 80 by removing the floating dead cells 13 which were the unnecessary living cells 12b. The flow cytometer 10 is preferably provided with a separation and collection mechanism for separating and collecting only the stem cells 12a which are the target living cells in the collection container 80, by separating and taking out the cells which floats in the sample liquid without attaching to the inner wall surface of the collection container 80, as the dead cells 13.

Additionally, when a culture processing, in which the living cells are cultivable, is executed for the sample liquid in the collection container 80, only the living cells in the sample liquid are cultured (propagated) without culturing (propagating) the dead cells which were the unnecessary living cells 12b in the sample liquid. Thus, the unnecessary living cells 12b in the sample group 11 are reliably caused to become the dead cells by the application of the pulsed voltage. Therefore, it is possible to separate and culture only the stem cells 12a in the sample group 11 by executing the culture processing for the sample liquid. Accordingly, it is possible to reduce the ratio of the dead cells 13 in the sample liquid. With the culture processing, it is possible to obtain a cell group in which almost all the cells are stem cells 12a. The flow cytometer 10 is preferably provided with a culture device of this type, making it possible to execute the culture processing to the sample liquid in the collection container 80 in which the living cells are cultivable. The flow cytometer 10 is configured as described above.

According to the flow cytometer having a cell sort function of the present invention, it is possible to highly accurately separate the unnecessary living cells from a group of the living cells, including the large amount of living cells, in a short period of time without damaging the target living cells at all, and cause the unnecessary living cells to become the dead cells by damaging them. Additionally, according to an aspect of the cell sorting method of the present invention, it is possible to highly accurately separate and collect the target living cells from a group of the living cells, including the large amount of living cells, in a short period of time without damaging the target living cells at all. Furthermore, according to another aspect of the cell sorting method of the present invention, it is possible to highly accurately separate the target living cells from a group of the living cells, including the large amount of living cells, and culture the separated target living cells in a short period of time without damaging the target living cells at all.

In the aforementioned embodiment, the living cells are caused to become the dead cells by applying the pulsed electric field to the living cells through the application of the pulsed voltage to the area between the electrodes. In the present invention, an electric field may be controlled to be applied to the portion of the sample liquid corresponding to the unnecessary living cells, or to be applied to the liquid itself, for instance. For example, when the intensity of the electric field to be generated in the area between the electrodes 64a and 64b is set to be extremely large, that is, $1.0 \times 10^3$ to $1.0 \times 10^4$ (V), electric discharge is generated in the sheath liquid and the sample liquid. Accordingly, a shock wave is generated in the sample liquid, for instance. If the shock wave destroys (irreversibly destroys) the cell membrane of the unnecessary living cell 12b, the unnecessary living cell 12b is caused to become the dead cell. Additionally, when a further extremely strong electric field acts on the sample liquid, the sample liquid enters a plasma state and an ultraviolet ray is generated. It is possible to damage the cell nuclei 88 of the unnecessary living cell 12b and even the DNA by the ultraviolet ray. In the present invention, the unnecessary living cell may be thus caused to become the dead cell by applying the pulsed electric field to the sample liquid itself.

The flow cytometer having a cell sorting function and the cell sorting method have been explained in detail. However, the present invention is not limited to the aforementioned embodiment. A variety of changes and modifications are obviously allowed for the aforementioned embodiment without departing from the scope of the present invention.

What is claimed is:

1. A living cell sorting method, comprising the steps of:
   forming a sample liquid flow including a group of living cells including target living cells, the living cells flowing in a line and kept away from each other;
   irradiating measurement light toward the sample liquid flow;
   obtaining light information from either of scattered light or fluorescence which is emitted by each of the living cells in the sample liquid flow when each of the living cells receives irradiation of the measurement light;
   determining, based on the light information obtained in the obtaining step, whether each of the living cells corresponding to the light information is among either the target living cells or not, and
   killing each of the living cells other than the target living cells, in response to a result of the determining step, by generating a pulsed electric field at a portion of the sample liquid flow corresponding to each of the living cells other than the target living cells,
   the pulsed electric field being formed between a pair of first electrodes to which pulsed voltage is applied, wherein
   the position of the first electrodes is disposed downstream of an irradiation position of the measurement light in the flow direction, and wherein a length along the flow direction of the sample liquid that is exposed to the pulsed electric field is controlled by a pair of second electrodes provided outside the pair of first electrodes.

2. The living cell sorting method according to claim 1, wherein each of the living cells other than the target living cells is killed by applying the pulsed electric field to each of the living cells other than the target living cells.

3. The living cell sorting method according to claim 2, wherein, the pulsed electric field applied to each of the living cells other than the target living cells is configured to have pulse width for damaging DNA (deoxyribonucleic acid) in a cell nuclei of each of the living cells other than the target living cells by applying the pulsed electric field to the cell nuclei.

4. The living cell sorting method according to claim 3, wherein the pulse width is less than $1.0 \times 10^{-6}$ second.

5. The living cell sorting method according to claim 4, wherein each of the living cells other than the target living cells is induced to apoptosis by Joule heat of pulsed electric current generated in each of the living cells by applying the pulsed electric field to each of the living cells other than the target living cells.

6. The living cell sorting method according to claim 2, wherein the field strength of the pulsed electric field applied to each of the living cells other than the target living cells, has pulse width and peak voltage for irreversibly destroying a cell membrane of each of the living cells other than the target living cells, under a condition that the field strength of an electric field applied to a cell membrane is stronger than the field strength of an electric field applied to a cell nuclei of each of the living cells other than the target living cells.

7. The living cell sorting method according to claim 6, wherein the pulse width is equal to or greater than $1.0 \times 10^{-6}$ second.

8. The living cell sorting method according to claim 7, wherein the field strength of the electric field applied to the cell membrane of each of the living cells other than the target living cells is equal to or greater than 1 kV/cm, and the peak voltage is equal to or greater than 10V.

9. The living cell sorting method according to claim 1, further comprising the steps of:
   collecting the sample liquid in a collection container after the pulsed voltage is applied, the sample liquid including the target living cells and dead cells obtained from applying the pulsed voltage; and
   separating and taking out the dead cells floating in the sample liquid without attaching to a surface of an inner wall of the collection container and simultaneously collecting the target living cells attaching to the surface of the inner wall of the collection container in the sample liquid.

10. The living cell sorting method according to claim 1, further comprising the steps of:
   collecting the sample liquid in a collection container after the pulsed voltage is applied, the sample liquid including the target living cells and the dead cells obtained from applying the pulsed voltage; and
   reducing dead cell ratio of the sample liquid by culturing only the target living cells in the sample liquid by executing a culture processing to the sample liquid in the collection container, the culturing processing being capable of culturing the living cells.

11. The living cell sorting method according to claim 1, wherein
   the first electrodes and the second electrodes are disposed in remote positions from the sample liquid.

12. The living cell sorting method according to claim 1, wherein
   the direction of the electric field formed by the first electrodes intersects with the flow direction of the sample liquid.

13. The living cell sorting method according to claim 1, wherein
   the direction of the electric field formed by the first electrodes is opposite to the direction of the electric field formed by the second electrodes.

14. The living cell sorting method according to claim 1, wherein
   the second electrodes prevent extension of the pulsed electric field along the flow direction of the sample liquid.

15. The living cell sorting method according to claim 1, wherein
   the length along the flow direction of the sample liquid that is exposed to the pulsed electric field is smaller than $1.0 \times 10^{-3}$ m.

* * * * *